United States Patent [19]
Payne et al.

[11] Patent Number: 5,489,432
[45] Date of Patent: Feb. 6, 1996

[54] BACILLUS THURINGIENSIS ISOLATES ACTIVE AGAINST COCKROACHES AND GENES ENCODING COCKROACH-ACTIVE TOXINS

[75] Inventors: Jewel M. Payne, San Diego, Calif.; M. Keith Kennedy, Racine, Wis.; John B. Randall, Racine, Wis.; David O. Brower, Racine, Wis.; H. Ernest Schnepf, San Diego, Calif.

[73] Assignee: Mycogen Corporation, San Diego, Calif.

[21] Appl. No.: 129,609

[22] Filed: Sep. 30, 1993

Related U.S. Application Data

[63] Continuation-in-part of Ser. No. 958,551, Oct. 19, 1992, Pat. No. 5,302,387, which is a continuation-in-part of Ser. No. 788,654, Nov. 6, 1991, abandoned.

[51] Int. Cl.$^6$ .......................... A01N 25/00; A01N 63/00
[52] U.S. Cl. .......................................... 424/405; 424/93.461
[58] Field of Search .................... 424/93 L, 94.6, 424/405, 93.461; 536/27; 530/350; 514/2

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 424/80 |
| 4,797,276 | 1/1989 | Herrnstadt et al. | 435/69.1 |
| 4,849,217 | 7/1989 | Soares et al. | 424/93.461 |
| 4,853,331 | 8/1989 | Herrnstadt et al. | 424/93.461 |
| 4,918,006 | 4/1990 | Ellar et al. | 424/93.461 |
| 4,948,734 | 8/1990 | Edwards et al. | 424/93.461 |
| 5,151,363 | 9/1992 | Payne | 435/252.3 |

OTHER PUBLICATIONS

Gaertner, Fran, and Leo Kim (1988) "Current Applied Recombinant DNA Projects" TIBTECH 3(4):S4–S7.
Gaertner, Frank (1990) "Cellular delivery systems for insecticidal proteins: living and non–living microorganisms" Controlled Delievery of Crop–Protection Agents, Richard W. Wilkins, ed., pp. 245–257.
Couch, Terry L. (1980) "Mosquito Pathogenicity of Bacillus thuringiensis var. israelensis" Developments in Industrial Microbiology 22:61–76.
Beegle, Clayton C. (1978) "Use of Entomogenous Bacteria in Agroccosystsms" Developments in Industrial Microbiology 20:97–104.
Krieg, Von A., A. M. Huger, G. A. Langenbruch and W. Schnetter (1983) "*Bacillus thurngiensis* var. tenebrionis: ein neuer, gegenuber Larven von Coleopteren wirksamer Pathotyp" Z. ang. Ent. 96:500–508.
Hofte, Herman, and H. R. Whiteley (1989) "Insecticidal Crystal Proteins of *Bacillus thurngiensis*" Microbiological Reviews 53(2):242–255.
Prefontaine, Gabrielle, Paul Fast, Pater C. K. Lau, Mary A. Hefford, Zaher Hanna and Roland Brousseau (1987) "Use of Oliogonucleotide Probes to Study the Relatedness of Delta–Endotoxin Genes among *Bacillus thuringiensis* Subspecies and Strains" Applied and Environmental Microbiology 53(12):2808–2814.
Feitelson, Jerald S., Jewel Payne and Leo Kim (1992) "*Bacillus thurngiensis:* Insects and Beyond" Bio/Technology 10:271–275.
Schnepf, H. Ernest, and H. R. Whiteley (1981) "Cloning and expression of the *Bacillus thurngiensis* crystal protein gene in *Escherichia coli*" Proc. Natl. Acad. Sci. USA 78(5):2893–2897.

Primary Examiner—Mindy Fleisher
Assistant Examiner—D. Schmickel
Attorney, Agent, or Firm—Saliwanchik & Saliwanchik

[57] ABSTRACT

The subject invention concerns a novel microbe and genes encoding novel toxin proteins with activity against cockroaches. Cockroaches are common house pests, and they create problems in hospitals, the food industry and in agriculture. The novel *Bacillus thuringiensis* microbe of the invention is referred to as *B.t.* PS185L8. The subject invention also concerns the use of *B.t.* PS201T6 to control cockroaches. A truncated form of a toxin obtained from PS201T6 having particular activity to cockroaches is also claimed for use in controlling the pest. The spores or crystals of the two microbes, or mutants thereof, are useful to control cockroaches in various environments. The genes of the invention can be used to transform various hosts wherein the novel toxic proteins can be expressed.

2 Claims, No Drawings

BACILLUS THURINGIENSIS ISOLATES ACTIVE AGAINST COCKROACHES AND GENES ENCODING COCKROACH-ACTIVE TOXINS

CROSS-REFERENCE TO A RELATED APPLICATION

This is a continuation-in-part of application Ser. No. 07/958,551, filed Oct. 19, 1992, now U.S. Pat. No. 5,302, 387 which is a continuation-in-part of application Ser. No. 07/788,654, filed Nov. 6, 1991, now abandoned.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] TIBTECH 6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* var. *kurstaki* have been used for many years as commercial insecticides for lepidopteran pests. For example, *B. thuringiensis* var. *kurstaki* HD-1 produces a crystal called a delta endotoxin which is toxic to the larvae of a number of lepidopteran insects.

In recent years, however, investigators have discovered *B.t.* pesticides with specificities for a much broader range of pests. For example, other species of *B.t.*, namely *B.t.* var. *israelensis* and *B.t.* var. *tenebrionis* (a.k.a. M-7, a.k.a. *B.t.* var. *san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and the beetle *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). Prefontaine et al. describe probes useful in classifying lepidopteran-active genes (Prefontaine, G., P. Fast, P. C. K. Lau, M. A. Hefford, Z. Hanna, R. Brosseau [1987] *Appl. Environ. Microbiol.* 53(12):2808–2814). The discovery of strains specifically toxic to other pests has been reported. (Feitelson, J. S., J. Payne, L. Kim [1992] Bio/Technology 10:271–275).

The cloning and expression of a *B.t.* crystal protein gene in *Escherichia coli* has been described in the published literature (Schnepf, H. E., H. R. Whitely [1981] *Proc. Natl. Acad. Sci. U.S.A.* 78:2893–2897). U.S. Pat. No. 4,448,885 and U.S. Pat. No. 4,467,036 both disclose the expression of *B.t.* crystal proteins in *E. coli*. U.S. Pat. Nos. 4,797,276 and 4,853,331 disclose *B. thuringiensis* var. *tenebrionis* (a.k.a. *B.t.* san diego, a.k.a. M-7) which can be used to control coleopteran pests in various environments. U.S. Pat. No. 4,918,006 discloses *B.t.* isolates active against Dipteran pests. U.S. Pat. No. 4,849,217 discloses *B.t.* isolates which have activity against the alfalfa weevil. U.S. Pat. No. 5,151, 363 and U.S. Pat. No. 4,948,734 disclose certain isolates of *B.t.* which have activity against nematodes. As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

Cockroaches such as the German cockroach (*Blatella germanica*), Oriental cockroach (*Blatta orientalis*), American cockroach (*Periplaneta americana*) and Brown cockroach (*Periplaneta americana*) are some of the most important insect pests to infest homes and commercial structures. These pests have omnivorous feeding habits resulting in the destruction of food, leather and fabrics. Cockroaches have also been implicated in the transmission of the disease-causing organisms Salmonella and Toxoplasma. Additionally, cockroaches contain allergins, to which approximately 7.5 percent of the human population are sensitive.

Cockroaches are frequently controlled with insecticidal baits. Because these baits are used in homes and restaurants, cockroach insecticides must be safe to humans. The heavy use of synthetic insecticides has resulted in the selection of resistant cockroach populations. New insecticides, safe for use around humans, are necessary to control these resistant populations.

BRIEF SUMMARY OF THE INVENTION

In one embodiment, the subject invention concerns a cockroach-active *Bacillus thuringiensis* (*B.t.*) isolate known as PS201T6, and DNA therefrom, which encodes novel cockroach-active protein toxins. The subject invention also includes variants of the *B.t.* isolate which have substantially the same pesticidal properties as the exemplified isolate. These variants would include mutants. Procedures for making mutants are well known in the microbiological art. Ultraviolet light and nitrosoguanidine are used extensively toward this end.

The subject invention further concerns the use of *B.t.* isolate PS201T6, and variants thereof, to control cockroaches. Cockroaches may be controlled using the PS201T6 isolate itself, variants of PS201T6, toxins obtained from said isolate, or toxins produced by DNA of said isolate wherein said DNA has been transformed into another host.

Further, the invention also includes the treatment of substantially intact cells of either a *B.t.* isolate or recombinant cells containing DNA from an isolate, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

A further aspect of the subject invention is the discovery of truncated forms of the 30 kDa PS201T6 toxin which are particularly active against cockroaches. A specific example is the truncated toxin which has about 43 amino acids removed from the N-terminus is about 25 kDa.

BRIEF DESCRIPTION OF THE SEQUENCES

SEQ ID NO. 1 is an oligonucleotide probe used according to the subject invention.

SEQ ID NO. 2 is a B.t. primer used according to the subject invention.

SEQ ID NO. 3 is a 3' reverse oligonucleotide primer used according to the subject invention.

SEQ ID NO. 4 is a gene-specific primer used according to the subject invention.

SEQ ID NO. 5 is a promoter sequence-primer used according to the subject invention.

SEQ ID NO. 6 is the nucleotide sequence encoding an approximately 30 kDa toxin of PS201T6.

SEQ ID NO. 7 is the deduced amino acid sequence of an approximately 30 kDa toxin of PS201T6.

SEQ ID NO. 8 is the amino acid sequence of a truncated 201T6 toxin of about 25 kDa.

SEQ ID NO. 9 is the N-terminal amino acid sequence of the 30 kDa 201T6 toxin.

SEQ ID NO. 10 is an internal amino acid sequence for the 30 kDa 201T6 toxin.

DETAILED DISCLOSURE OF THE INVENTION

The *Bacillus thuringiensis* isolate PS201T6 has the following characteristics in its biologically pure form:

TABLE 1

| Comparison of B.t. PS201T6, and B.t. HD-1 | | |
|---|---|---|
| | B.t. PS201T6 | B.t. HD-1 |
| Inclusions: | elliptical & bipyramid | bipyramid |
| Approximate molecular wt. of proteins by SDS-PAGE | 133,000 31,000 | 130,000 68,000 |
| Host range | Cockroaches Diptera Corn Rootworm | Lepidoptera |

The cultures disclosed in this application have been deposited in the Agricultural Research Service Patent Culture Collection (NRRL), Northern Regional Research Center, 1815 North University Street, Peoria, Ill. 61604, U.S.A.

| Culture | Repository No. | Deposit date |
|---|---|---|
| *Bacillus thuringiensis* | NRRL B-18750 | January 9, 1991 |

-continued

| Culture | Repository No. | Deposit date |
|---|---|---|
| PS201T6 | | |
| E. coli NM522 (pMYC2362) | NRRL B-21018 | December 2, 1992 |
| E. coli NM522 (pMYC2357) | NRRL B-21017 | December 2, 1992 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Genes and Toxins

The genes and toxins useful according to the subject invention include not only the full length sequences disclosed but also fragments of these sequences, variants, mutants, and fusion proteins which retain the characteristic pesticidal activity of the toxins specifically exemplified. As used herein, the terms "variants" or "variations" of genes refer to nucleotide sequences which code for the same toxins or which code for equivalent toxins having pesticidal activity. As used herein, the term "equivalent toxins" refers to toxins having the same or essentially the same biological activity against the target pests as the claimed toxins.

It should be apparent to a person skilled in this art that genes coding for cockroach-active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining cockroach activity are also included in this definition.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention further comprises variant or equivalent toxins (and nucleotide sequences coding for equivalent toxins) having the same or essentially the same pesticidal activity of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to actMty or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant Hosts

The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested by the pest. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the pest's habitat. Microorganism hosts may also live symbiotically with a specific species of cockroach. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the habitat of the cockroach. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, e.g., genera Metarhizium, Saccharomyces, Cryptococcus, Kluyveromyces, Sporobolomyces, Rhodotorula, and Aureobasidium. Of particular interest are such bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of Cells

As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids, and Helly's fixative (See: Humason, Gretchen L., *Animal Tissue Techniques,* W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like. Methods for treatment of microbial cells are disclosed in U.S. Pat Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bio-availability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of Cells

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations

Formulated bait granules containing an attractant and spores and crystals of the *B.t.* isolates, or recombinant microbes comprising the genes obtainable from the *B.t.* isolates disclosed herein, can be applied to the environment of the cockroach. The bait may be applied liberally since the toxin does not affect animals or humans. Product may also be formulated as a spray or powder. Cockroaches pick the product up on their feet or abdomen and carry it back to the nest where other cockroaches will be exposed to the toxin.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the cockroaches, e.g., baseboards, walls, floors, by spraying, dusting, sprinkling, baiting, or the like.

Mutants

Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolate

A subculture of the B.t. isolate can be used to inoculate the following medium, a peptone, glucose, salts medium.

| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Purification and Amino Acid Sequencing

A Bacillus thuringiensis (B.t.) can be cultured as described in Example 1 or by using other standard media and fermentation techniques well known in the art. Delta-endotoxin can be isolated and purified by harvesting toxin protein inclusions by standard sedimentation centrifugation. The recovered protein inclusions can be partially purified by sodium bromide (28–38%) isopycnic gradient centrifugation (Pfannenstiel, M. A., E. J. Ross, V. C. Kramer, K. W. Nickerson [1984] FEMS Microbiol. Lett. 21:39). Thereafter the individual toxin proteins can be resolved by solubilizing the crystalline protein complex in an alkali buffer and fractionating the individual proteins by DEAE-sepharose CL-6B (Sigma Chem. Co., St. Louis, Mo.) chromatography by step-wise increments of increasing concentrations of an NaCl-containing buffer (Reichenberg, D., in Ion Exchangers in Organic and Biochemistry [C. Calmon and T. R. E. Kressman, eds.], Interscience, New York, 1957).

Fractions containing the 30 kDa 201T6 toxin were bound to PVDF membrane (Millipore, Bedford, Mass.) by Western blotting techniques (Towbin, H., T. Staehelin, K. Gordon [1979] Proc. Natl. Acad. Sci. U.S.A. 76:4350) and the N-terminal amino acid sequence was determined by the standard Edman reaction with an automated gas-phase sequenator (Hunkapiller, M. W., R. M. Hewick, W. L. Dreyer, L. E. Hood [1983] Meth. Enzymol. 91:399). The sequence obtained was: $NH_2$- MKESIYYNEE-$CO_2H$ (SEQ ID NO. 9).

From this sequence data an oligonucleotide probe was designed by utilizing a codon frequency table assembled from available sequence data of other B.t. toxin genes. The oliogonucleotide probe corresponding to the N-terminal amino acid sequence of SEQ ID NO. 9 is 5' ATG AAA GAA (T/A) (G/C) (T/A) AT (T/A) TAT TAT ATT GAA GA-3'(SEQ ID NO. 10). The probes can be synthesized on an Applied Biosystems, Inc. DNA synthesis machine.

EXAMPLE 3

Molecular Cloning and Expression of Toxin Genes from Bacillus thuringiensis Strain PS201T6

Total cellular DNA was prepared from Bacillus thuringiensis (B.t.) PS201T6 cells grown to an optical density, at 600 nm, of 1.0. Cells were pelleted by centrifugation and resuspended in protoplast buffer (20 mg/ml lysozyme in 0.3M sucrose, 25 mM Tris-Cl (pH 8.0), 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 µg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

RFLP analyses were performed by standard hybridization of Southern blots of PS201T6 DNA digested with various restriction endonucleases. An oligonucleotide probe deduced from the amino acid sequence of the 30 kDa toxin was used to detect the gene encoding this polypeptide. The sequence of this probe was: 5'-GACTGGATCC ATGAAA-GAA(T or A) (G or C)(T or A)AT(T or A)TATTA TAAT-GAAGA-3' (SEQ ID NO. 1). This probe was mixed at four positions and contained a 5' BamHI cloning site. Hybridizing bands included an approximately 4.0 kbp EcoRI fragment and an approximately 2.7 kbp EcoRV fragment.

A 285 bp probe for detection of the 130 kDa toxin gene was obtained by polymerase chain reaction (PCR) amplification from 201T6 cellular DNA using a B.t. "universal" forward primer and a reverse oligonucleotide primer. The sequence of the B.t. universal primer is: 5'-GGACCAGGAT TTACAGGAGG AGAT-3' (SEQ ID NO. 2). The sequence of the reverse primer is: 5'-TGGAATAAATTCAATT(C or T)(T or G)(A or G)TC(T or A)A-3' (SEQ ID NO. 3). The amplified DNA fragment was radiolabelled with $^{32}$P-dATP using a BMB (Indianapolis, Ind.) random priming kit. Southern blot analyses of PS201T6 DNA with this probe revealed hybridizing bands that included an approximately 9.3 kbp HindIII fragment and two EcoRI fragments approximately 1.8 and 4.5 kbp in size.

A gene library was constructed from PS201T6 DNA partially digested with Sau3A. Partial restriction digests were fractionated by agarose gel electrophoresis. DNA fragments 9.3 to 23 kbp in size were excised from the gel, electroeluted from the gel slice, purified on an Elutip D ion exchange column (Schleicher and Schuell, Keene, N.H.), and recovered by ethanol precipitation. The Sau3A inserts were ligated into BamHI-digested LambdaGem-11 (Promega, Madison, Wis.). Recombinant phage were packaged and plated on *E. coli* KW251 cells. Plaques were screened by hybridization with the probes described above. Hybridizing phage were plaque-purified and used to infect liquid cultures of *E. coli* KW25 1 cells for isolation of DNA by standard procedures (Maniatis et al., supra).

For subcloning the gene encoding the 30 kDa toxin gene, preparative amounts of phage DNA were digested with EcoRI and electrophoresed on an agarose gel. The approximately 4.5 kbp band containing the toxin gene was excised from the gel, electroeluted from the gel slice, and purified by anion exchange chromatography as above. The purified DNA insert was ligated into EcoRI-digested pBluescript K/S (Stratagene, La Jolla, Calif.). The ligation mix was used to transform frozen, competent *E. coli* NM522 cells (ATCC 47000). Transformants were plated on LB agar containing 100 μg/ml ampicillin, 1 mM IPTG, and 0.5 mM XGAL. Plasmids were purified from putative recombinants by alkaline lysis (Maniatis et al., supra) and analyzed by restriction endonuclease digestion and agarose gel electrophoresis. The desired plasmid construct pMYC2357 contains a toxin gene that is novel compared to other toxin genes encoding insecticidal proteins.

Sequence analysis of the toxin gene revealed that it encodes a protein of 29,906 daltons, deduced from the DNA sequence. The nucleotide and deduced amino acid sequences are shown in SEQ ID NOS. 6 and 7, respectively.

The gene encoding the 30 kDa was expressed under control of the p52A1 promoter and ribosome binding site in the vector, pBClac (an *E. coli/B. thuringiensis* shuttle vector comprised of the replication origin from pBC16 (Bernhard, K. et al. [1978] *J. Bacteriol.* 133:897–903) and pUC19 (Yanisch-Perron, C. et al. [1985] *Gene* 33:103–119). The 30 kDa open reading frame and 3' flanking sequences were amplified by PCR using a forward oligonucleotide complementary to the 5' end of the gene and a reverse oligonucleotide complementary to the T7 promoter region of pBluescript. The sequence of the gene-specific primer was: 5'-GGAATTCCTC ATG AAA GAG TCA ATT TAC TAC A-3' (SEQ ID NO. 4). This primer contained a 5' BspHI cloning site. The p52A1 promoter/rbs sequences were amplified using a promoter-specific primer and a vector primer from pMYC2321. The sequence of promoter-specific primer was 5'-GTAAACATGT TCATACCACC TTTTTFAA-3' (SEQ ID NO. 5). This primer contained a 5' AflIII cloning site. The p52A1 promoter fragment (digested with BamHI and AflIII), the 30 kDa toxin gene fragment (digested with BspHI and SalI) and pBClac (digested with BamHi and SalI) were ligated together to generate pMYC2358. This construct was introduced into the acrystalliferous (Cry$^-$) *B.t.* host, CryB (A. Aronson, Purdue University, West Lafayette, Ind.) by electroporation. Expression of the 30 kDa toxin was demonstrated by SDS-PAGE analysis. NaBr-purified crystals were prepared (Pfannenstiel et al., supra).

For subcloning the 130 kDa toxin, preparative amounts of phage DNA were digested with SalI and electrophoresed on an agarose gel. The approximately 12.8 kbp band containing the toxin gene was excised from the gel, electroeluted from the gel slice, and purified by ion exchange chromatography as described above. The purified DNA insert was ligated into an XhoI-digested pHTBlueII (an *E. coli/B. thuringiensis* shuttle vector comprised of pBluescript S/K (Stratagene, La Jolla, Calif.) and the replication origin from a resident *B.t.* plasmid (Lereclus et al., supra). The ligation mix was used to transform frozen, competent *E. coli* NM522 cells (ATCC 47000). β-galactosidase transformants were screened by restriction digestion of alkaline lysate plasmid minipreps as above. The desired plasmid construct, pMYC2362, contains a gene encoding a 130kDa toxin that is novel compared to other toxin genes encoding pesticidal proteins.

pMYC2362 was introduced into the acrystalliferous (Cry$^-$) *B.t.* host, CryB (A. Aronson, Purdue University, West Lafayette, Ind.), by electropotation. Expression of the 130 kDa toxin was demonstrated by SDS-PAGE analysis. NaBr-purified cyrstals were prepared as above.

EXAMPLE 4

Testing of *B.t.* Isolate PS201T6

The spore-crystal pellet of *B.t.* strain PS201T6 was suspended in 0.1M $Na_2CO_3$ buffer, pH 11, containing 0.5% β -mercaptoethanol. The suspension was left at room temperature for i hour, followed by dialysis against 15 volumes of 0.1M $Na_2CO_3$ buffer, pH 9.5 at room temperature for 3 hours. This aqueous suspension was fed to the German cockroach, *Blatella germanica,* ad lib. *B.t.* strain PS201T6 caused 78% mortality 21 days post-treatment, with control mortality below 3%.

EXAMPLE 5

Pronase Processing of PS201T6 Culture Material

Pronase is a commercially-available enzyme preparation which can be used to proteolytically degrade *B.t.* toxin compositions to assess the activity of toxin fragments. The 133 kDa protein from PS201T6 was hydrolyzed to low molecular weight peptides. Surprisingly, the 30 kDa toxin from PS201T6 was digested to a limit peptide of approximately 25 kDa after Pronase treatment as described herein.

Cultures of PS201T6 were harvested by centifugation and resuspended in about ⅙th to 1/25th of their original culture volume in 0.1M $Na_2CO_3/NaHCO_3$ (pH 11.0) containing 0.5 mg/ml Pronase E (Sigma Chemical Company, P-5147 type XIV bacterial Protease from *Streptomyces griseus*). The suspension was incubated at 37° C. overnight with mixing.

Suspensions were dialyzed against 2 changes of 50 to 100 volumes each of either distilled water or 0.1M Na₂CO₃/NaHCO3 (pH 9.5) to yield dialyzed suspensions.

The suspension resulting from the 0.1M Na₂CO₃/NaHCO3 (pH 9.5) dialysis was centrifuged to remove cells, spores and debris. Additional purification from spores and debris was accomplished by filtration through Whatman glass microfibre filters, 0.8 micron cellulose acetate filters and 0.2 micron cellulose acetate filters to yield a filtered supernatant.

Dialyzed suspensions and filtered supernatants can be further dialyzed against 2 changes of 50 to 100 volumes distilled water, followed by lyophilization to yield lyophilized samples.

The 25 kDa fragment was found to have high activity against cockroaches.

EXAMPLE 6

Activated Toxins from PS201T6

The removal of 43 amino acids from the N-terminus of the 201T6 30 kDa toxin was found to result in an advantageous activation of this toxin which increased the scope and potency of its activity. The sequence of the truncated toxin is shown in SEQ ID NO. 8. Table 3 compares the physical properties of the truncated toxin and the full length 30 kDa toxin. The truncated toxin was found to have advantageous biological activity. Removal of 43 amino acids can be accomplished by treatment with trypsion or other appropriate enzyme or enzyme mixture such as Pronase. Other biologically active fragments could be obtained by those skilled in the art using the teachings provided herein.

TABLE 3

| | 201T6 - 30 kDa | Activated 201T6 - 25 kDa |
|---|---|---|
| Molecular Weight | 29,906 | 24,782 |
| Isolectric Point | 4.92 | 4.91 |
| Extinction Coefficient | 26,150 | 21,680 |

Further, the removal of about 1 to about 12 additional amino acids from the N-terminus can also be done to obtain an activated toxin. It is also possible to remove about 5 to 10 amino acids from the C-terminus.

EXAMPLE 7

Activity of the Truncated 30 kDa Toxin from PS201T6 Against Cockroaches

Compositions used to treat cockroaches were prepared by four methods (A–D). These four compositions were used in assays to determine the activity of the 30 kDa 201T6 toxin and truncated toxins against the German cockroach, *Blatella germanica*. The four methods are as follows:

A—The 30 kDa toxin was isolated and purified as described in Example 2.

B—A bacterial cell pellet was resuspended in about 1/10 of the original culture volume in 0.1M sodium phosphate (pH 7.0) with 0.5 mg/ml Pronase E (Sigma Chemical Company, P-5147 type XIV bacterial Protease from *Streptomyces grisius*) and incubated for 3 hours at 37° C., followed by dialysis against 0.1M sodium carbonate (pH 9.5).

C—A bacterial cell pellet was resuspended in about 1/10 of the original culture volume in 0.1M sodium carbonate (pH 11.0) with 0.5 mg/ml Pronase E and incubated for 24 hours at 37° C., followed by dialysis against 0.1M sodium carbonate (pH 9.5).

D—A cell pellet was resuspended in about 1/20 of the original culture volume in 0.1M sodium phosphate (pH 11.0) with 0.5 mg/ml Pronase E and incubated for 24 hours at 37° C., followed by dialysis against 0.1M sodium carbonate (pH 9.5). The material was sterile filtered through a 0.22 μm membrane to remove vegetative cells and spores.

As discussed above, Pronase is a commercially-available enzyme preparation which is used here to treat PS201T6 protein compositions in order to asses the activity of fragments of the protein.

The results of these experiments are shown in Table 4.

TABLE 4

| Treatment | % mortality after 21 days |
|---|---|
| A | 6 |
| B | 90, 82, 98, 46, 96 |
| C | 86, 100, 80 |
| D | 100, 76 |
| control, buffer only | 2 |

EXAMPLE 8

Cloning of Novel *B.t.* Genes Into Insect Viruses

A number of viruses are known to infect insects. These viruses include, for example, baculoviruses and entomopoxviruses. In one embodiment of the subject invention, cockroach-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A purified toxin active against cockroaches, said toxin produced in a culture of *Bacillus thuringiensis* isolate PS201T6, having the activity against cockroaches characteristic of NRRL B-18750; wherein said toxin)as a molecular weight of less than about 31 kD and comprises the amino acid sequence shown in SEQ .ID NO. 8, or a cockroach-active fragment thereof.

2. The toxin, according to claim 1, that consists of the amino acid sequence shown in SEQ ID NO. 8.

\* \* \* \* \*

UNITED STATES PATENT AND TRADEMARK OFFICE
CERTIFICATE OF CORRECTION

PATENT NO. : 5,489,432
DATED : February 6, 1996
INVENTOR(S) : Jewel M. Payne, M. Keith Kennedy, John B. Randall, David O. Brower, H. Ernest Schnepf It is certified that error appears in the above-indentified patent and that said Letters Patent is hereby corrected as shown below:

Column 2: line 56: "fight" should read --light--.
Column 5: line 61: "actMty" should read --activity--.
Column 10: line 24: "-CO$_2$H" should read --CO$_2$H--.
Column 12: line 4: "TTTTTFAA-3'" should read --TTTTTAA-3'--; line 8: "BamHi" should read --BamHI--; line 33: "electropotation" should read --electroporation--; line 44: "i hour," should read --1 hour,--.
Column 13: line 5: "NaHCO3" should read --NaHCO$_3$--.

Signed and Sealed this

Seventh Day of May, 1996

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GACTGGATCC ATGAAAGAAW SWATWTATTA TAATGAAGA        39

( 2 ) INFORMATION FOR SEQ ID NO:2:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGACCAGGAT TTACAGGAGG AGAT        24

( 2 ) INFORMATION FOR SEQ ID NO:3:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

TGGAATAAAT TCAATTYKRT CWA        23

( 2 ) INFORMATION FOR SEQ ID NO:4:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

GGAATTCCTC ATGAAAGAGT CAATTTACTA C        31

( 2 ) INFORMATION FOR SEQ ID NO:5:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

GTAAACATGT TCATACCACC TTTTTAA        27

( 2 ) INFORMATION FOR SEQ ID NO:6:

( i ) SEQUENCE CHARACTERISTICS:

( A ) LENGTH: 795 base pairs
              ( B ) TYPE: nucleic acid
              ( C ) STRANDEDNESS: double
              ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
              ( A ) ORGANISM: Bacillus thuringiensis
              ( B ) STRAIN: neoleoensis
              ( C ) INDIVIDUAL ISOLATE: PS201T6

( v i i ) IMMEDIATE SOURCE:
              ( A ) LIBRARY: LambdaGem (TM)-11 library of Kenneth E. Narva
              ( B ) CLONE: 201T635

( x i ) SEQUENCE DESCRIPTION: SEQ ID NO:6:

| | | | | | | |
|---|---|---|---|---|---|---|
| ATGAAAGAGT | CAATTTACTA | CAATGAAGAA | AATGAAATAC | AAATTTCACA | AGGAAACTGT | 60 |
| TTCCCAGAAG | AATTAGGACA | TAATCCTTGG | AGACAACCTC | AATCCACAGC | AAGAGTTATT | 120 |
| TATTTAAAAG | TAAAAGATCC | TATTGATACT | ACTCAATTAT | TAGAAATAAC | AGAAATCGAA | 180 |
| AATCCCAATT | ATGTATTACA | AGCTATTCAA | CTAGCTGCTG | CCTTCCAAGA | TGCATTAGTA | 240 |
| CCAACTGAAA | CAGAATTTGG | AGAAGCCATT | AGATTTAGTA | TGCCTAAAGG | ATTAGAAGTT | 300 |
| GCAAAAACTA | TTCAACCTAA | GGGTGCTGTT | GTTGCTTACA | CAGATCAAAC | TCTGTCACAA | 360 |
| AGCAACAACC | AAGTTAGTGT | TATGATTGAT | AGAGTTATTA | GTGTTTTAAA | AACTGTAATG | 420 |
| GGAGTAGCTC | TTAGTGGTTC | CATTATAACT | CAATTAACAG | CTGCTATCAC | TGATACTTTT | 480 |
| ACAAACCTTA | ATACACAAAA | AGATTCTGCT | TGGGTTTTTT | GGGGAAAAGA | AACTTCACAT | 540 |
| CAAACAAATT | ACACATATAA | TGTCATGTTT | GCAATTCAAA | ATGAAACAAC | TGGACGCGTA | 600 |
| ATGATGTGTG | TACCTATTGG | ATTTGAAATT | AGAGTATTTA | CTGATAAAAG | AACAGTTTTA | 660 |
| TTTTTAACAA | CTAAAGATTA | CGCTAATTAT | AGTGTGAATA | TTCAAACCCT | AAGGTTTGCT | 720 |
| CAACCACTTA | TTGATAGCAG | AGCACTTTCA | ATTAATGATT | TATCAGAAGC | ACTTAGATCT | 780 |
| TCTAAATATT | TATAC | | | | | 795 |

( 2 ) INFORMATION FOR SEQ ID NO:7:

( i ) SEQUENCE CHARACTERISTICS:
              ( A ) LENGTH: 265 amino acids
              ( B ) TYPE: amino acid
              ( C ) STRANDEDNESS: single
              ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
              ( A ) ORGANISM: Bacillus thuringiensis
              ( B ) STRAIN: neoleoensis
              ( C ) INDIVIDUAL ISOLATE: PS201T6

( v i i ) IMMEDIATE SOURCE:
              ( A ) LIBRARY: LambdaGem (TM)-11 Library of Kenneth E. Narva
              ( B ) CLONE: 201T635

( x i ) SEQUENCE DESCRIPTION: SEQ ID NO:7:

| Met | Lys | Glu | Ser | Ile | Tyr | Tyr | Asn | Glu | Glu | Asn | Glu | Ile | Gln | Ile | Ser |
|---|---|---|---|---|---|---|---|---|---|---|---|---|---|---|---|
| 1 | | | | 5 | | | | | 10 | | | | | 15 | |

| Gln | Gly | Asn | Cys | Phe | Pro | Glu | Glu | Leu | Gly | His | Asn | Pro | Trp | Arg | Gln |

|     |     |     |     | 20  |     |     |     | 25  |     |     |     | 30  |     |     |
| --- | --- | --- | --- | --- | --- | --- | --- | --- | --- | --- | --- | --- | --- | --- |
| Pro | Gln | Ser<br>35 | Thr | Ala | Arg | Val | Ile<br>40 | Tyr | Leu | Lys | Val<br>45 | Lys | Asp | Pro | Ile |
| Asp | Thr<br>50 | Thr | Gln | Leu | Leu | Glu<br>55 | Ile | Thr | Glu | Ile<br>60 | Glu | Asn | Pro | Asn | Tyr |
| Val<br>65 | Leu | Gln | Ala | Ile<br>70 | Gln | Leu | Ala | Ala | Ala<br>75 | Phe | Gln | Asp | Ala | Leu | Val<br>80 |
| Pro | Thr | Glu | Thr | Glu<br>85 | Phe | Gly | Glu | Ala | Ile<br>90 | Arg | Phe | Ser | Met | Pro<br>95 | Lys |
| Gly | Leu | Glu | Val<br>100 | Ala | Lys | Thr | Ile | Gln<br>105 | Pro | Lys | Gly | Ala | Val<br>110 | Val | Ala |
| Tyr | Thr | Asp<br>115 | Gln | Thr | Leu | Ser | Gln<br>120 | Ser | Asn | Asn | Gln | Val<br>125 | Ser | Val | Met |
| Ile | Asp<br>130 | Arg | Val | Ile | Ser | Val<br>135 | Leu | Lys | Thr | Val | Met<br>140 | Gly | Val | Ala | Leu |
| Ser<br>145 | Gly | Ser | Ile | Ile | Thr<br>150 | Gln | Leu | Thr | Ala | Ala<br>155 | Ile | Thr | Asp | Thr | Phe<br>160 |
| Thr | Asn | Leu | Asn | Thr<br>165 | Gln | Lys | Asp | Ser | Ala<br>170 | Trp | Val | Phe | Trp | Gly<br>175 | Lys |
| Glu | Thr | Ser | His<br>180 | Gln | Thr | Asn | Tyr | Thr<br>185 | Tyr | Asn | Val | Met | Phe<br>190 | Ala | Ile |
| Gln | Asn | Glu<br>195 | Thr | Thr | Gly | Arg | Val<br>200 | Met | Met | Cys | Val | Pro<br>205 | Ile | Gly | Phe |
| Glu | Ile | Arg<br>210 | Val | Phe | Thr | Asp | Lys<br>215 | Arg | Thr | Val | Leu | Phe<br>220 | Leu | Thr | Thr |
| Lys<br>225 | Asp | Tyr | Ala | Asn | Tyr<br>230 | Ser | Val | Asn | Ile | Gln<br>235 | Thr | Leu | Arg | Phe | Ala<br>240 |
| Gln | Pro | Leu | Ile | Asp<br>245 | Ser | Arg | Ala | Leu | Ser<br>250 | Ile | Asn | Asp | Leu | Ser<br>255 | Glu |
| Ala | Leu | Arg | Ser<br>260 | Ser | Lys | Tyr | Leu | Tyr<br>265 |     |     |     |     |     |     |     |

( 2 ) INFORMATION FOR SEQ ID NO:8:

( i ) SEQUENCE CHARACTERISTICS:
        ( A ) LENGTH: 222 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Bacillus thuringiensis
        ( B ) STRAIN: neoleoensis
        ( C ) INDIVIDUAL ISOLATE: PS201T6

( x i ) SEQUENCE DESCRIPTION: SEQ ID NO:8:

| Val<br>1 | Lys | Asp | Pro | Ile<br>5 | Asp | Thr | Thr | Gln | Leu<br>10 | Leu | Glu | Ile | Thr | Glu<br>15 | Ile |
| --- | --- | --- | --- | --- | --- | --- | --- | --- | --- | --- | --- | --- | --- | --- | --- |
| Glu | Asn | Pro | Asn<br>20 | Tyr | Val | Leu | Gln | Ala<br>25 | Ile | Gln | Leu | Ala | Ala<br>30 | Ala | Phe |
| Gln | Asp | Ala<br>35 | Leu | Val | Pro | Thr | Glu<br>40 | Thr | Glu | Phe | Gly | Glu<br>45 | Ala | Ile | Arg |
| Phe | Ser | Met<br>50 | Pro | Lys | Gly | Leu | Glu<br>55 | Val | Ala | Lys | Thr | Ile<br>60 | Gln | Pro | Lys |

| | | | | | | | | | | | | | | |
|---|---|---|---|---|---|---|---|---|---|---|---|---|---|---|
| Gly 65 | Ala | Val | Val | Ala | Tyr 70 | Thr | Asp | Gln | Thr | Leu 75 | Ser | Gln | Ser | Asn | Asn 80 |
| Gln | Val | Ser | Val | Met 85 | Ile | Asp | Arg | Val | Ile 90 | Ser | Val | Leu | Lys | Thr 95 | Val |
| Met | Gly | Val | Ala 100 | Leu | Ser | Gly | Ser | Ile 105 | Ile | Thr | Gln | Leu | Thr 110 | Ala | Ala |
| Ile | Thr | Asp 115 | Thr | Phe | Thr | Asn | Leu 120 | Asn | Thr | Gln | Lys | Asp 125 | Ser | Ala | Trp |
| Val | Phe 130 | Trp | Gly | Lys | Glu | Thr 135 | Ser | His | Gln | Thr | Asn 140 | Tyr | Thr | Tyr | Asn |
| Val 145 | Met | Phe | Ala | Ile | Gln 150 | Asn | Glu | Thr | Thr | Gly 155 | Arg | Val | Met | Met | Cys 160 |
| Val | Pro | Ile | Gly | Phe 165 | Glu | Ile | Arg | Val | Phe 170 | Thr | Asp | Lys | Arg | Thr 175 | Val |
| Leu | Phe | Leu | Thr 180 | Thr | Lys | Asp | Tyr | Ala 185 | Asn | Tyr | Ser | Val | Asn 190 | Ile | Gln |
| Thr | Leu | Arg 195 | Phe | Ala | Gln | Pro | Leu 200 | Ile | Asp | Ser | Arg | Ala 205 | Leu | Ser | Ile |
| Asn | Asp 210 | Leu | Ser | Glu | Ala | Leu 215 | Arg | Ser | Ser | Lys | Tyr 220 | Leu | Tyr | | |

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Met Lys Glu Ser Ile Tyr Tyr Asn Glu Glu
1           5                   10

(2) INFORMATION FOR SEQ ID NO:10:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:10:

ATGAAAGAAW SWATWTATTA TATTGAAGA        29